(12) United States Patent
Wang et al.

(10) Patent No.: US 9,840,511 B2
(45) Date of Patent: Dec. 12, 2017

(54) 2-(ARYL OR HETEROARYL-)PHENYL (AZA)BENZOFURAN COMPOUNDS FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Zhongxing Zhang, Madison, CT (US); John F. Kadow, Wallingford, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 0 days.

(21) Appl. No.: 15/312,022

(22) PCT Filed: May 19, 2015

(86) PCT No.: PCT/US2015/031569
§ 371 (c)(1),
(2) Date: Nov. 17, 2016

(87) PCT Pub. No.: WO2015/179392
PCT Pub. Date: Nov. 26, 2015

(65) Prior Publication Data
US 2017/0101416 A1    Apr. 13, 2017

Related U.S. Application Data

(60) Provisional application No. 62/001,243, filed on May 21, 2014.

(51) Int. Cl.
| | | |
|---|---|---|
| C07D 307/78 | (2006.01) | |
| C07D 491/048 | (2006.01) | |
| C07D 405/10 | (2006.01) | |
| C07D 307/84 | (2006.01) | |

(52) U.S. Cl.
CPC ....... *C07D 491/048* (2013.01); *C07D 307/84* (2013.01); *C07D 405/10* (2013.01)

(58) Field of Classification Search
CPC . C07D 307/78; C07D 491/048; C07D 405/10
USPC ................................. 549/462, 115; 514/302
See application file for complete search history.

(56) References Cited

U.S. PATENT DOCUMENTS

| 8,445,497 B2 | 5/2013 | Yeung et al. |
| 8,871,759 B2 | 10/2014 | Coburn et al. |
| 9,090,661 B2 | 7/2015 | Coburn et al. |
| 2012/0328569 A1 | 12/2012 | McComas et al. |

FOREIGN PATENT DOCUMENTS

| WO | WO2007/039146 A1 | 4/2007 |
| WO | 2012/003164 | * 1/2012 |

* cited by examiner

*Primary Examiner* — Niloofar Rahmani
(74) *Attorney, Agent, or Firm* — James Epperson

(57) ABSTRACT

Compounds of Formula I, including their salts, as well as compositions and methods of using the compounds are set forth. The compounds have activity against hepatitis C virus (HCV) and may be useful in treating those infected with HCV: formula (I).

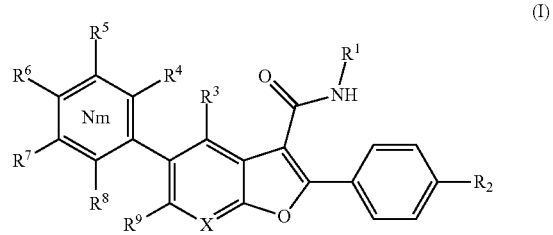

17 Claims, No Drawings

2-(ARYL OR HETEROARYL-)PHENYL (AZA)BENZOFURAN COMPOUNDS FOR THE TREATMENT OF HEPATITIS C

CROSS REFERENCE TO RELATED APPLICATION

This non-provisional application claims the benefit of U.S. Provisional Application Ser. No. 62/001,243 filed May 21, 2014 which is herein incorporated by reference in its entirety.

FIELD OF THE INVENTION

The invention relates to novel compounds, including their salts, which have activity against hepatitis C virus (HCV) and which are useful in treating those infected with HCV. The invention also relates to compositions and methods of making and using these compounds.

BACKGROUND OF THE INVENTION

Hepatitis C virus (HCV) is a major human pathogen, infecting an estimated 170 million persons worldwide-roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N. Engl. J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, has shown an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed; see for example, WO2009/101022, as well as WO 2012/058125.

What is therefore needed in the art are additional compounds which are novel and are effective against hepatitis C. Additionally, these compounds should provide advantages for pharmaceutical uses, for example, with regard to one or more of their mechanism of action, binding, inhibition efficacy, target selectivity, solubility, safety profiles, and/or bioavailability. Also needed are new formulations and methods of treatment which utilize these compounds.

SUMMARY OF THE INVENTION

One aspect of the invention is a compound of Formula I including pharmaceutically acceptable salts thereof:

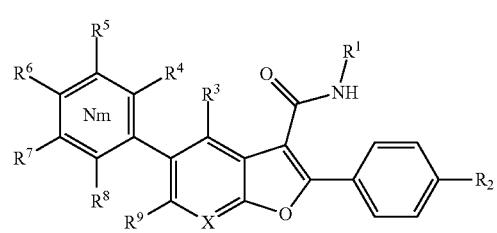

wherein
m is 0 or 1;
X is N or C—$R^{10}$;
$R^1$ is methyl;
$R^2$ is $Ar^1$;

$Ar^1$ is phenyl, 5-membered heteroaryl or 6-membered heteroaryl, and is substituted with 0-3 substituents selected from the group of cyano, halo, alkyl, cycloalkyl, haloalkyl, OH, $OR^{101}$, haloalkoxy, $NH_2$, $NR^{102}R^{103}$, $COOR^{102}R^{103}$, $S(O)_2NR^{102}R^{103}$, and $NR^{101}CONR^{102}R^{103}$;

$R^{101}$ is hydrogen, alkyl or cycloalkyl with 0-3 substituents selected from halo, hydroxyl, alkoxy, and haloalkoxy;

$R^{102}$, $R^{103}$ are each independently hydrogen, alkyl or cycloalkyl with 0-3 substituents selected from halo, hydroxyl, alkoxy, and haloalkoxy; or $R^{102}$ and $R^{103}$ can form a ring by joining two atoms, one from each of $R^{102}$ and $R^{103}$;

$R^3$ is hydrogen, halo, or alkyl;

$R^4$, $R^5$, $R^6$, $R^7$, $R^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, $COOR^{201}$ and $CON(R^{202})(R^{203})$;

$R^{201}$ is hydrogen, alkyl or cycloalkyl with 0-3 substituents selected from halo, hydroxyl, alkoxy, and haloalkoxy;

$R^{202}$, $R^{203}$ are each independently selected from the group of hydrogen, alkyl, cycloalkyl, alkenyl, cycloalkyl alkynyl, cyclic ether, cyclic amine, lactame, fused bicyclic alkyl, bridged bicyclic alkyl, spiro bicyclic alkyl, fused bicyclic ether, bridged bicyclic ether, spiro bicyclic ether, fused bicyclic amine, bridged bicyclic amine and spiro bicyclic amine, with 0-3 substituents selected from the group of halo, OH, $OR^{104}$, $NH_2$, $NR^{105}R^{106}$, $COOR^{104}$, $CONR^{105}R^{106}$, $S(O)_2R^{104}$, $S(O)_2NR^{105}R^{106}$, $NR^{104}CONR^{105}R^{106}$, $OR^{104}CONR^{105}R^{106}$, $C(=NR^{107})NR^{105}R^{106}$, $NR^{108}C(=NR^{107})NR^{105}R^{106}$, haloalkoxy, $Ar^2$, $O—Ar^2$, and $NR^{105}—Ar^2$; or $R^{202}$ and $R^{203}$ can form a ring by joining two atoms, one from each of $R^{202}$ and $R^{203}$;

$R^{202}$ and $R^{203}$ can also form bicyclic or tricyclic rings by joining multiple atoms from each of $R^{202}$ and $R^{203}$;

$R^{104}$ is hydrogen, alkyl or cycloalkyl with 0-3 substituents selected from halo, hydroxyl, alkoxy, and haloalkoxy;

$R^{105}$, $R^{106}$ are each independently hydrogen, alkyl or cycloalkyl with 0-3 substituents selected from halo, hydroxyl, alkoxy, and haloalkoxy; or $R^{105}R^{106}$ can form a ring by joining two atoms, one from each of $R^{105}$ and $R^{106}$;

$R^{107}$, $R^{108}$ are each independently hydrogen, alkyl or cycloalkyl with 0-3 substituents selected from halo, hydroxyl, alkoxy, and haloalkoxy; or $R^{107}$ and $R^{108}$ can form a ring by joining two atoms, one from each of $R^{107}$ and $R^{108}$;

$Ar^2$ is phenyl, 5-membered heteroaryl or 6-membered heteroaryl, and is substituted with 0-3 substituents selected from the group of cyano, halo, alkyl, cycloalkyl, haloalkyl, OH, $OR^{204}$, haloalkoxy, $NH_2$, $NR^{205}R^{206}$, $COOR^{204}$, $CONR^{205}R^{206}$, $S(O)_2R^{204}$, $S(O)_2NR^{205}R^{206}$, and $NR^{204}CONR^{205}R^{206}$;

$R^{204}$ is hydrogen, alkyl or cycloalkyl with 0-3 substituents selected from halo, hydroxyl, alkoxy, and haloalkoxy;

$R^{205}$, $R^{206}$ are each independently hydrogen, alkyl or cycloalkyl with 0-3 substituents selected from halo, hydroxyl, alkoxy, and haloalkoxy; or $R^{205}$ and $R^{206}$ can form a ring by joining two atoms, one from each of $R^{205}$ and $R^{206}$;

$R^9$ is selected from the group of hydrogen, halo, alkyl, haloalkyl, cycloalkyl, alkoxy, $Ar^3$ and $NR^{301}R^{302}$;

$R^{301}$ is selected from the group of hydrogen, alkyl, cycloalkyl, (cycloalkyl)alkyl, benzyl, alkylcarbonyl, haloalkyl carbonyl, phenyl carbonyl, (alkoxyphenyl)carbonyl, alkylsulfonyl, phenylsulfonyl, (alkoxyphenyl)sulfonyl and (haloalkoxyphenyl)sulfonyl;

$R^{302}$ is hydrogen, alkyl, hydroxyalkyl, or alkoxyalkyl; or $R^{301}$ and $R^{302}$ taken together with the nitrogen to which they are attached is oxazolidinonyl or dioxothiazinyl;

$Ar^3$ is phenyl, 5-membered heteroaryl or 6-membered heteroaryl, and is substituted with 0-3 substituents selected from cyano, halo, alkyl, cycloalkyl, haloalkyl, OH, $OR^{303}$, haloalkoxy, $NH_2$, $NR^{304}R^{305}$, $COOR^{303}$, $CONR^{304}R^{305}$, $S(O)_2R^{303}$, $S(O)_2NR^{304}R^{305}$, and $NR^{303}CONR^{304}R^{305}$;

$R^{303}$ is hydrogen, alkyl or cycloalkyl with 0-3 substituents selected from halo, hydroxyl, alkoxy, and haloalkoxy;

$R^{304}$, $R^{305}$ are each independently hydrogen, alkyl or cycloalkyl with 0-3 substituents selected from halo, hydroxyl, alkoxy, and haloalkoxy; or $R^{304}$ and $R^{305}$ can form a ring by joining two atoms, one from each of $R^{304}$ and $R^{305}$;

$R^{10}$ is hydrogen, alkyl, halo, $N(R^{401})(R^{402})$, or alkylsulfonyl;

$R^{401}$ and $R^{402}$ are each independently selected from the group of hydrogen, alkyl, hydroxyalkyl, alkoxyalkyl, alkylsulfonyl, and alkylsulfonylalkyl;

or $N(R^{401})(R^{402})$ taken together is azetidinyl, pyrrolidinyl, piperidinyl, or piperazinyl, and is substituted with 0-2 substituents selected from alkyl, hydroxyalkyl, and hydroxy.

The invention also relates to pharmaceutical compositions comprising a compound of Formula I, including a pharmaceutically acceptable salt thereof, and a pharmaceutically acceptable carrier, excipient and/or diluent.

In addition, the invention provides one or more methods of treating hepatitis C infection comprising administering a therapeutically effective amount of a compound of Formula I to a patient.

Also provided as part of the invention are one or more methods for making the compounds of Formula I.

The present invention is directed to these, as well as other important ends, hereinafter described.

DETAILED DESCRIPTION OF THE EMBODIMENTS

As used herein, the singular forms "a", "an", and "the" include plural reference unless the context specifically dictates otherwise.

Unless otherwise specifically set forth elsewhere in the application, the following terms may be used herein and shall have the following meanings: "Hydrogen" or "H" refers to hydrogen, including its isotopes, such as deuterium. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a fourto six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to one or more compounds of Formula I, including pharmaceutically acceptable salts thereof:

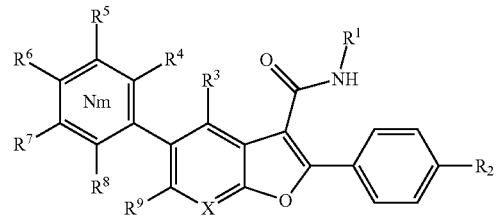

wherein
m is 0 or 1;
X is N or C—$R^{10}$;
$R^1$ is methyl;
$R^2$ is $Ar^1$;
$Ar^1$ is phenyl, 5-membered heteroaryl or 6-membered heteroaryl, and is substituted with 0-3 substituents selected from the group of cyano, halo, alkyl, cycloalkyl, haloalkyl, OH, $OR^{101}$, haloalkoxy, $NH_2$, $NR^{102}R^{103}$, $COOR^{101}$, $CONR^{102}R^{103}$, $S(O)_2R^{101}$, $S(O)_2NR^{102}R^{103}$, and $NR^{101}CONR^{102}R^{103}$;
$R^{101}$ is hydrogen, alkyl or cycloalkyl with 0-3 substituents selected from halo, hydroxyl, alkoxy, and haloalkoxy;
$R^{102}$, $R^{103}$ are each independently hydrogen, alkyl or cycloalkyl with 0-3 substituents selected from halo, hydroxyl, alkoxy, and haloalkoxy; or
$R^{102}$ and $R^{103}$ can form a ring by joining two atoms, one from each of $R^{102}$ and $R^{103}$;
$R^3$ is hydrogen, halo, or alkyl;
$R^4$, $R^5$, $R^6$, $R^7$, $R^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, $COOR^{201}$ and $CON(R^{202})(R^{203})$;
$R^{201}$ is hydrogen, alkyl or cycloalkyl with 0-3 substituents selected from halo, hydroxyl, alkoxy, and haloalkoxy;
$R^{202}$, $R^{203}$ are each independently selected from the group of hydrogen, alkyl, cycloalkyl, alkenyl, cycloalkyl alkynyl, cyclic ether, cyclic amine, lactame, fused bicyclic alkyl, bridged bicyclic alkyl, spiro bicyclic alkyl, fused bicyclic ether, bridged bicyclic ether, spiro bicyclic ether, fused bicyclic amine, bridged bicyclic amine and spiro bicyclic amine, with 0-3 substituents selected from the group of halo, OH, $OR^{104}$, $NH_2$, $NR^{105}R^{106}$, $COOR^{104}$, $CONR^{105}R^{106}$, $S(O)_2R^{104}$, $S(O)_2NR^{105}R^{106}$, $NR^{104}CONR^{105}R^{106}$, $OR^{104}CONR^{105}R^{106}$, $C(=NR^{107})NR^{105}R^{106}$, $NR^{108}C(=NR^{107})NR^{105}R^{106}$, haloalkoxy, $Ar^5$, O—$Ar^2$, and $NR^{105}$—$Ar^2$; or
$R^{202}$ and $R^{203}$ can form a ring by joining two atoms, one from each of $R^{202}$ and $R^{203}$;
$R^{202}$ and $R^{203}$ can also form bicyclic or tricyclic rings by joining multiple atoms from each of $R^{202}$ and $R^{203}$;
$R^{104}$ is hydrogen, alkyl or cycloalkyl with 0-3 substituents selected from halo, hydroxyl, alkoxy, and haloalkoxy;
$R^{105}$, $R^{106}$ are each independently hydrogen, alkyl or cycloalkyl with 0-3 substituents selected from halo, hydroxyl, alkoxy, and haloalkoxy; or
$R^{105}$ and $R^{106}$ can form a ring by joining two atoms, one from each of $R^{105}$ and $R^{106}$;
$R^{107}$, $R^{108}$ are each independently hydrogen, alkyl or cycloalkyl with 0-3 substituents selected from halo, hydroxyl, alkoxy, and haloalkoxy; or
$R^{107}$ and $R^{108}$ can form a ring by joining two atoms, one from each of $R^{107}$ and $R^{108}$;

Ar² is phenyl, 5-membered heteroaryl or 6-membered heteroaryl, and is substituted with 0-3 substituents selected from the group of cyano, halo, alkyl, cycloalkyl, haloalkyl, OH, OR²⁰⁴, haloalkoxy, NH₂, NR²⁰⁵R²⁰⁶, COOR²⁰⁴, CONR²⁰⁵R²⁰⁶, S(O)₂R²⁰⁴, S(O)₂NR²⁰⁵R²⁰⁶, and NR²⁰⁴CONR²⁰⁵R²⁰⁶;

R²⁰⁴ is hydrogen, alkyl or cycloalkyl with 0-3 substituents selected from halo, hydroxyl, alkoxy, and haloalkoxy;

R²⁰⁵, R²⁰⁶ are each independently hydrogen, alkyl or cycloalkyl with 0-3 substituents selected from halo, hydroxyl, alkoxy, and haloalkoxy; or R²⁰⁵ and R²⁰⁶ can form a ring by joining two atoms, one from each of R²⁰⁵ and R²⁰⁶;

R⁹ is selected from the group of hydrogen, halo, alkyl, haloalkyl, cycloalkyl, alkoxy, Ar³ and NR³⁰¹R³⁰²;

R³⁰¹ is selected from the group of hydrogen, alkyl, cycloalkyl, (cycloalkyl)alkyl, benzyl, alkylcarbonyl, haloalkyl carbonyl, phenyl carbonyl, (alkoxyphenyl)carbonyl, alkylsulfonyl, phenylsulfonyl, (alkoxyphenyl)sulfonyl and (haloalkoxyphenyl)sulfonyl;

R³⁰² is hydrogen, alkyl, hydroxyalkyl, or alkoxyalkyl; or

R³⁰¹ and R³⁰² taken together with the nitrogen to which they are attached is oxazolidinonyl or dioxothiazinyl;

Ar³ is phenyl, 5-membered heteroaryl or 6-membered heteroaryl, and is substituted with 0-3 substituents selected from the group of cyano, halo, alkyl, cycloalkyl, haloalkyl, OH, OR³⁰³, haloalkoxy, NH₂, NR³⁰⁴R³⁰⁵, COOR³⁰³, CONR³⁰⁴R³⁰⁵, S(O)₂R³⁰³, S(O)₂NR³⁰⁴R³⁰⁵, and NR³⁰³CONR³⁰⁴R³⁰⁵;

R³⁰³ is hydrogen, alkyl or cycloalkyl with 0-3 substituents selected from halo, hydroxyl, alkoxy, and haloalkoxy;

R³⁰⁴, R³⁰⁵ are each independently hydrogen, alkyl or cycloalkyl with 0-3 substituents selected from halo, hydroxyl, alkoxy, and haloalkoxy; or R³⁰⁴ and R³⁰⁵ can form a ring by joining two atoms, one from each of R³⁰⁴ and R³⁰⁵;

R¹⁰ is hydrogen, alkyl, halo, N(R⁴⁰¹)(R⁴⁰²), or alkylsulfonyl;

R⁴⁰¹ and R⁴⁰² are independently selected from the group of hydrogen, alkyl, hydroxyalkyl, alkoxyalkyl, alkylsulfonyl, and alkylsulfonylalkyl;

or N(R⁴⁰¹)(R⁴⁰²) taken together is azetidinyl, pyrrolidinyl, piperidinyl, or piperazinyl, and is substituted with 0-2 substituents selected from alkyl, hydroxyalkyl, and hydroxy.

In a preferred embodiment of the invention, m is 0.

It is further preferred that R¹ is alkyl, and more preferably methyl.

It is also preferred that R⁴, R⁵, R⁶, R⁷, R⁸ are each selected from CON(R²⁰²)(R²⁰³). More preferably, R⁵ is CON(R²⁰²)(R²⁰³).

Additionally, it is preferred that R²⁰² and R²⁰³ are hydrogen or alkyl.

In certain embodiments it is also preferred that R² is a 5-membered heteroaryl group. More preferably, the heteroaryl group will contain 2 to 3 nitrogens.

It is also preferred that R⁹ is selected from the group of haloalkyl, Ar³ and NR³⁰¹R³⁰². The haloalkyl is preferably 1-3 fluoroalkyl, and more preferably is 1-3 fluoropropyl. In another embodiment, it is preferred that R⁹ is NR³⁰¹, and R³⁰¹ is selected from alkyl and alkylsulfonyl. In a further embodiment, it is preferred that Ar³ is substituted pyrazole.

R¹⁰ is preferably hydrogen.

Also preferred are compounds of Formula I, including pharmaceutically acceptable salts thereof, which are selected from the group of:

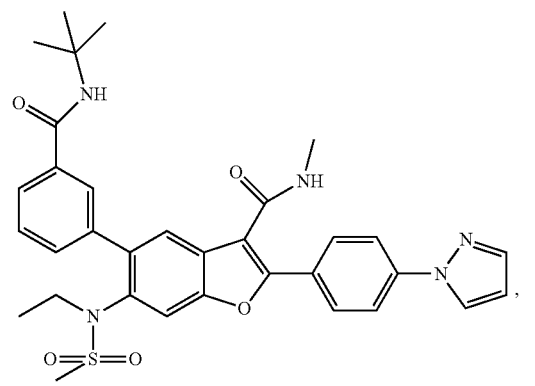

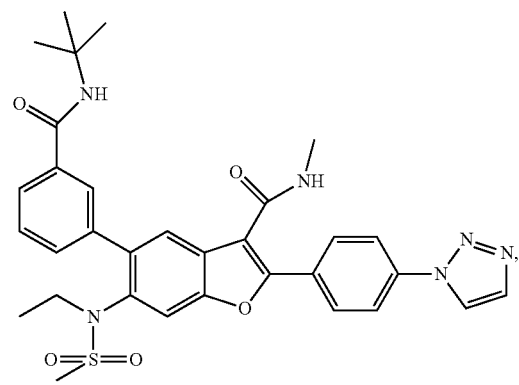

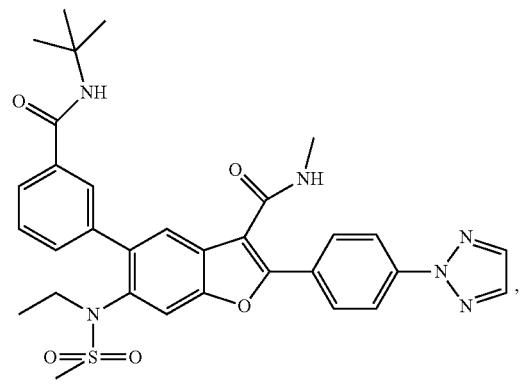

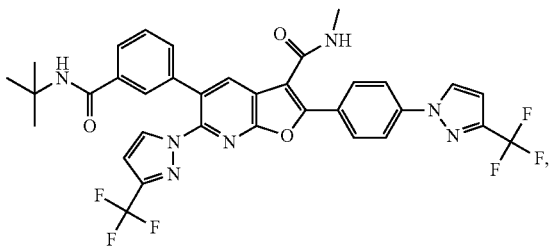

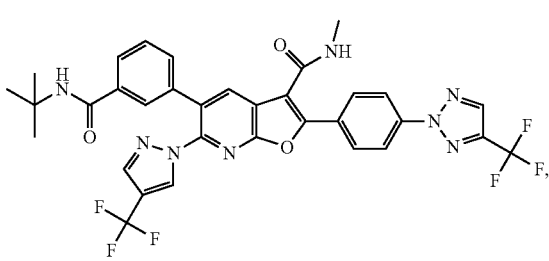

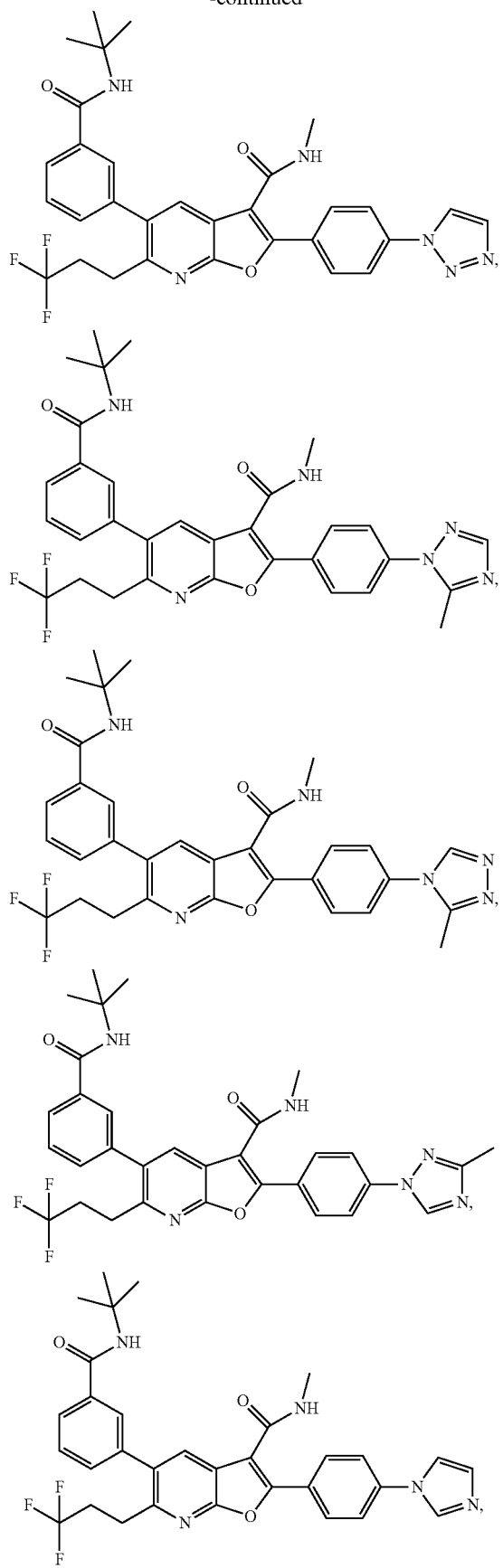
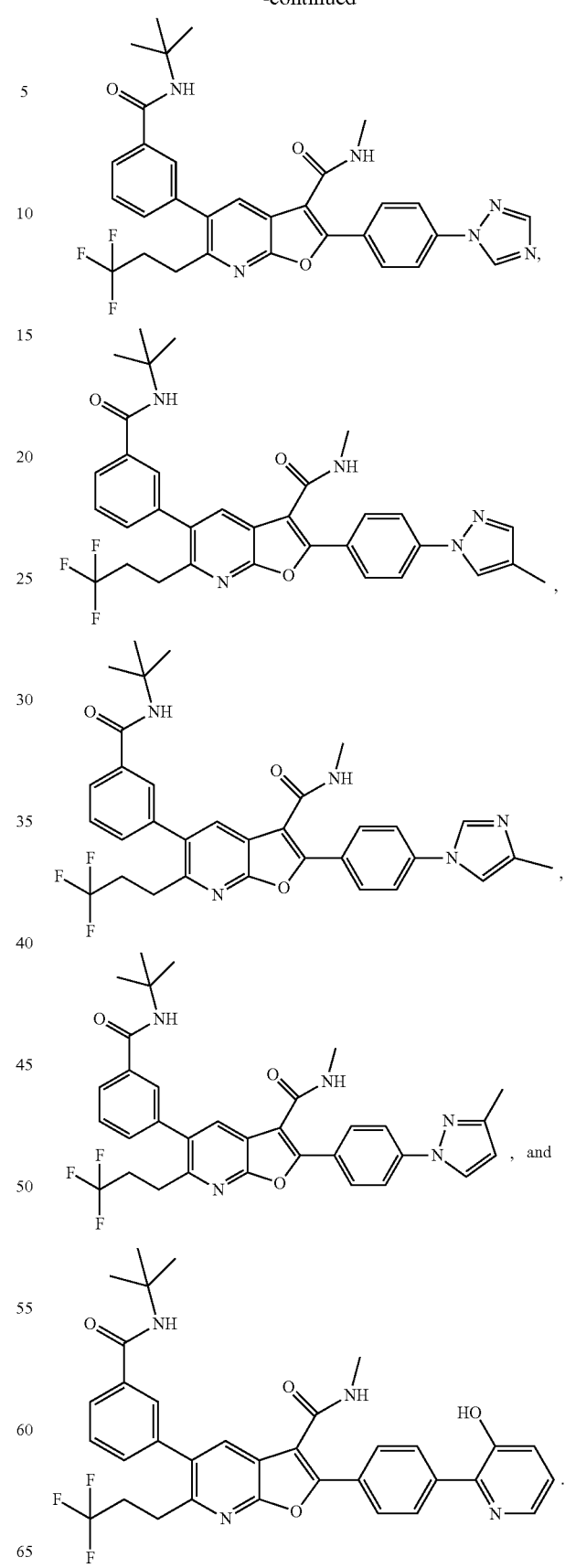

Also preferred are compounds of Formula I, including pharmaceutically acceptable salts thereof, which are selected from the group of:

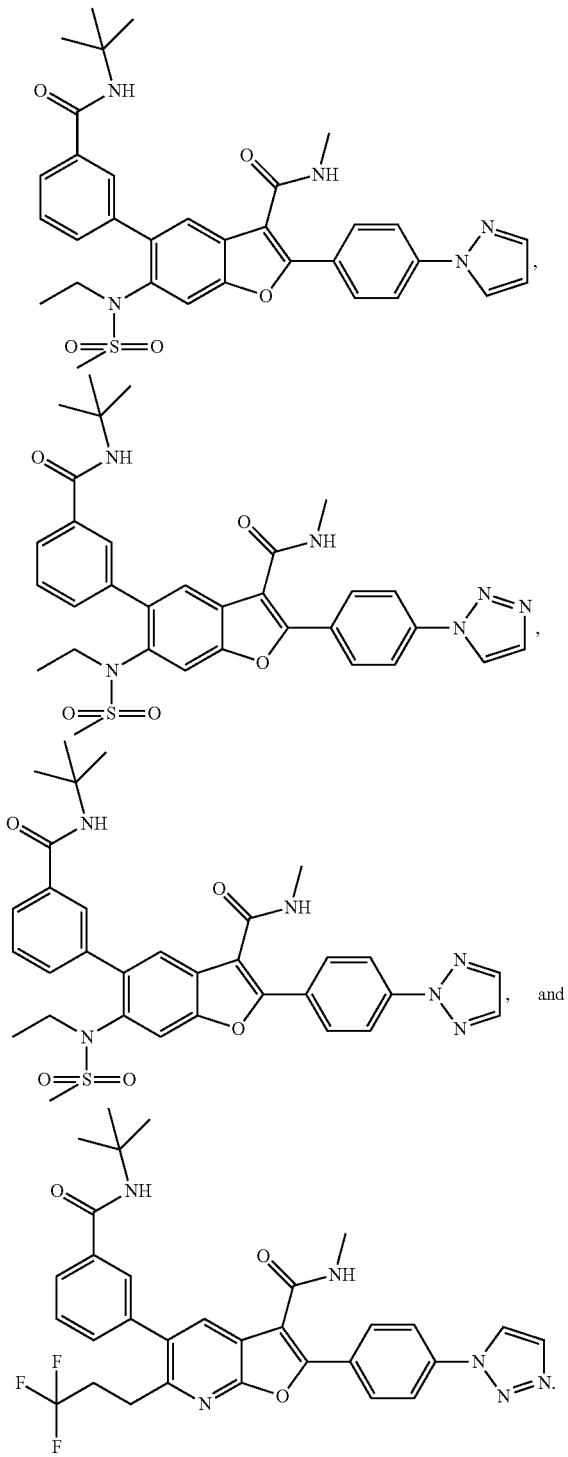

Pharmaceutical Compositions and Methods of Treatment

The compounds according to the various embodiments herein set forth demonstrate activity against HCV NS5B, and can be useful in treating HCV and HCV infection. Therefore, another aspect of the invention is a composition comprising a compound of Formula I, or a pharmaceutically acceptable salt thereof, and a pharmaceutically acceptable carrier, excipient and/or diluent.

Another aspect of the invention is a composition further comprising an additional compound having anti-HCV activity.

Another aspect of the invention is a composition where the compound having anti-HCV activity is an interferon or a ribavirin. Another aspect of the invention is wherein the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of Formula I, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of Formula I or a pharmaceutically acceptable salt thereof.

Another aspect of the invention is a method of inhibiting the function of the HCV NS5B protein comprising contacting the HCV NS5B protein with a compound of Formula I or a pharmaceutically acceptable salt thereof.

Another aspect of the invention is a method of treating an HCV infection in a patient comprising administering to the patient a therapeutically effective amount of a compound of Formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of Formula I, or a pharmaceutically acceptable salt thereof, in conjunction with (prior to, after, or concurrently) another compound having anti-HCV activity.

Another aspect of the invention is the method wherein the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method wherein the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method wherein the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of about 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be about 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods as part of the invention herein are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |

TABLE 1-continued

| Brand Name | Physiological Class | Type of Inhibitor or Target | Source Company |
|---|---|---|---|
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |

TABLE 1-continued

| Brand Name | Physiological Class | Type of Inhibitor or Target | Source Company |
|---|---|---|---|
| VCH-916 | Antiviral | NS5B Polymerase Inhibitor | ViroChem Pharma |
| GS-9190 | Antiviral | NS5B Polymerase Inhibitor | Gilead |
| Peg-interferon lambda | Antiviral | Interferon | ZymoGenetics/Bristol-Myers Squibb |

Synthesis Methods

The compounds may be made by methods available in the art, as well as those described below. Some reagents and intermediates are available in the art. Other reagents and intermediates can be made by methods available in the art using commercially available materials. The variables (e.g. numbered "R" substituents) used to describe the synthesis of the compounds are intended only to illustrate how to make these compounds, and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine.

For the section of compounds in the 0000 series all Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., compound isolation). Compounds purified by preparative HPLC were diluted in methanol (1.2 mL) and purified using a Shimadzu LC-8A or LC-10A or Dionex APS-3000 or Waters Acquity™ automated preparative HPLC system.

EXAMPLES

Preparation of Compound 1001:

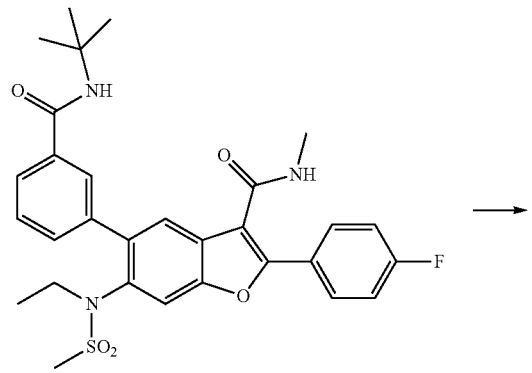

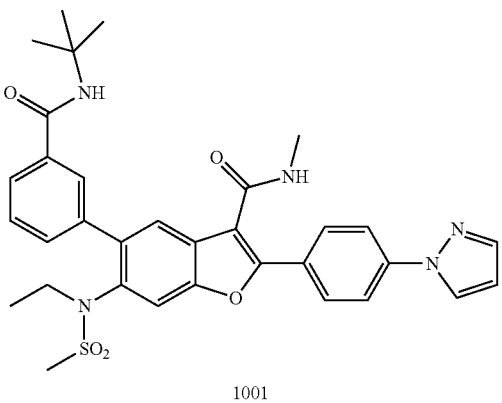

1001

A mixture of 1H-pyrazole (54.2 mg), 5-(3-(tert-butylcarbamoyl)phenyl)-6-(N-ethylmethylsulfonamido)-2-(4-fluorophenyl)-N-methylbenzofuran-3-carboxamide (15 mg), K$_2$CO$_3$ (14.66 mg) and copper (3.37 mg) was heated to 140° C. for 6 hours. The mixture was diluted with DMF and filtered to removed solid. The solution of mixture was subjected to purification by preparative HPLC system.

| 1001 | |
|---|---|
| MS (M + H)$^+$ Calcd. | 614.2 |
| MS (M + H)$^+$ Observ. | 614.2 |
| Retention Time | 1.35 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 1002 and 1003:

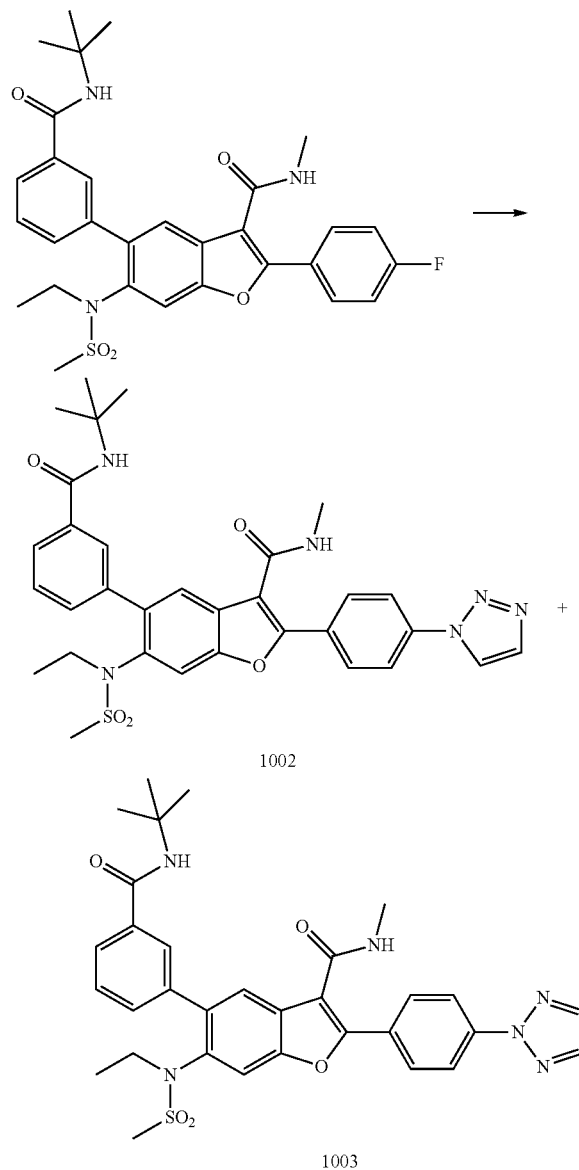

Compounds 1002 and 1003 were prepared via the same procedure towards compound 1001, using 1,2,3-triazole. LC condition for compounds 1002 and 1003 was the same for compound 100.

| 1002 | |
|---|---|
| MS (M + H)+ Calcd. | 615.2 |
| MS (M + H)+ Observ. | 615.2 |
| Retention Time | 1.18 min |

| 1003 | |
|---|---|
| MS (M + H)+ Calcd. | 615.2 |
| MS (M + H)+ Observ. | 615.2 |
| Retention Time | 1.20 min |

Preparation of Compound 2001:

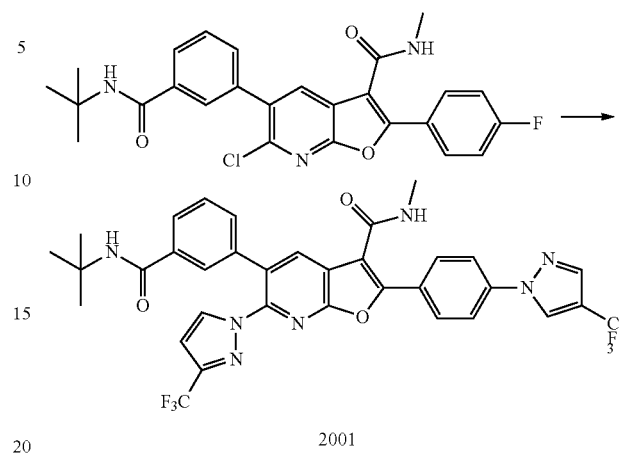

NaH (8.33 mg, 60%) was added into a solution of 5-(3-(tert-butylcarbamoyl)phenyl)-6-chloro-2-(4-fluorophenyl)-N-methylfuro[2,3-b]pyridine-3-carboxamide (10 mg) and 3-(trifluoromethyl)-1H-pyrazole (28.4 mg) in DMF. The reaction was heated at 85° C. for 24 hour. The product was isolated by preparative HPLC system.

| 2001 | |
|---|---|
| MS (M + H)+ Calcd. | 696.2 |
| MS (M + H)+ Observ. | 696.2 |
| Retention Time | 2.38 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 2002:

Compound 2002 were prepared via the same procedure towards compound 2001, using 4-(trifluoromethyl)-1H-pyrazole. LC condition for compound 2002 was the same for compound 2001.

2002

| | |
|---|---|
| MS (M + H)+ Calcd. | 696.2 |
| MS (M + H)+ Observ. | 696.2 |
| Retention Time | 2.40 min |

Preparation of Compound 3001:

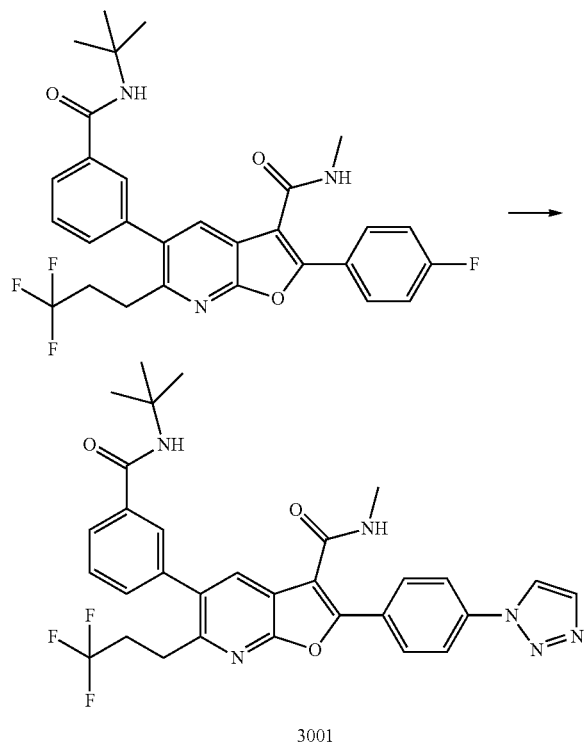

3001

A mixture of 1H-1,2,3-triazole (96 mg), 5-(3-(tert-butylcarbamoyl)phenyl)-2-(4-fluorophenyl)-N-methyl-6-(3,3,3-trifluoropropyl)furo[2,3-b]pyridine-3-carboxamide (15 mg), $K_2CO_3$ (11.48 mg) and copper (3.52 mg) was heated to 140° C. for 6 hours. The mixture was diluted with DMF and filtered to removed solid. The solution of mixture was subjected to purification by preparative HPLC system.

| 3001 | |
| --- | --- |
| MS (M + H)+ Calcd. | 591.2 |
| MS (M + H)+ Observ. | 591.2 |
| Retention Time | 1.63 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compounds 3002-3010 were prepared via the same procedure towards compound 3001, using the corresponding heterocycles. LC condition for compounds 3002-3010 was the same for compound 3001.

| Cmpd # | Structure | MS (M + H)+ Calcd. | MS (M + H)+ Observ. | Retention Time (min) |
| --- | --- | --- | --- | --- |
| 3002 | 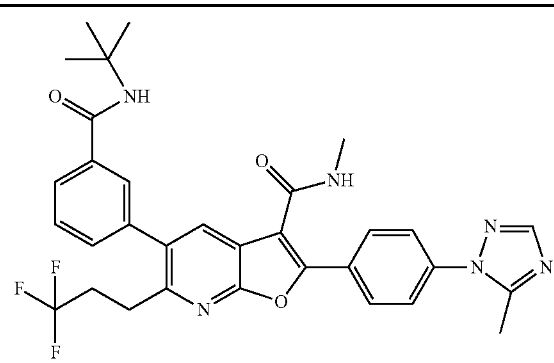 | 605.2 | 605.2 | 1.31 |
| 3003 | 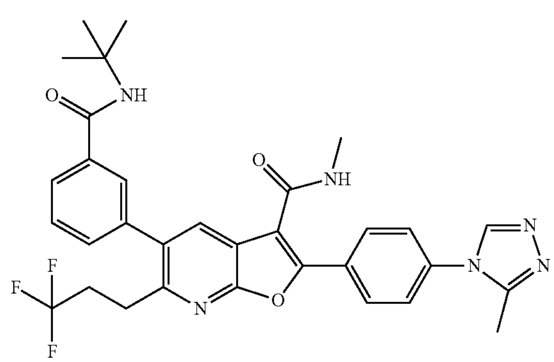 [SMILES: CNC(=O)c1c(-c2ccc(-n3cnnc3C)cc2)oc2nc(CCC(F)(F)F)c(-c3cccc(C(=O)NC(C)(C)C)c3)cc12] | 605.2 | 605.2 | 1.58 |

-continued

| Cmpd # | Structure | MS (M + H)+ Calcd. | MS (M + H)+ Observ. | Retention Time (min) |
|---|---|---|---|---|
| 3004 | 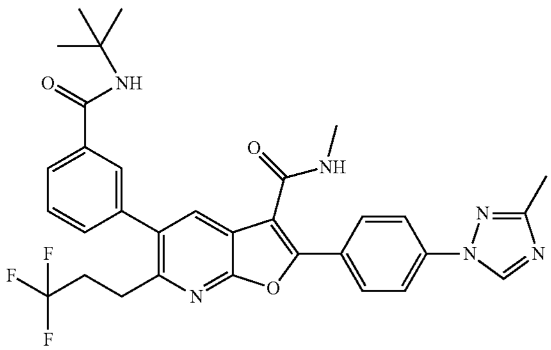 | 605.2 | 605.2 | 1.73 |
| 3005 | 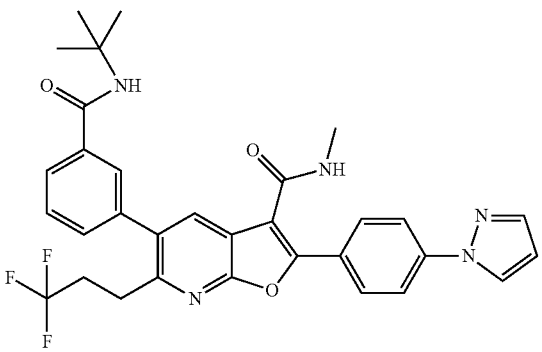 [SMILES: CNC(=O)c1c(-c2ccc(-n3cccn3)cc2)oc2nc(CCC(F)(F)F)c(-c3cccc(C(=O)NC(C)(C)C)c3)cc12] | 590.2 | 590.2 | 1.79 |
| 3006 | 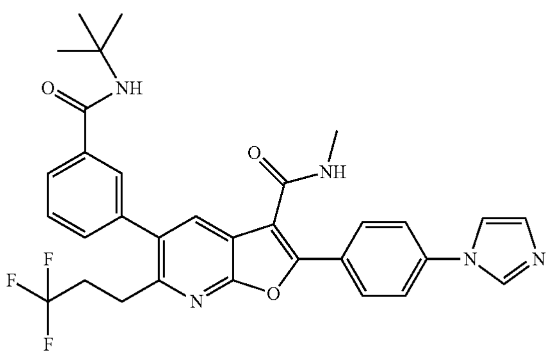 [SMILES: CNC(=O)c1c(-c2ccc(-n3ccnc3)cc2)oc2nc(CCC(F)(F)F)c(-c3cccc(C(=O)NC(C)(C)C)c3)cc12] | 590.2 | 590.2 | 1.08 |
| 3007 | 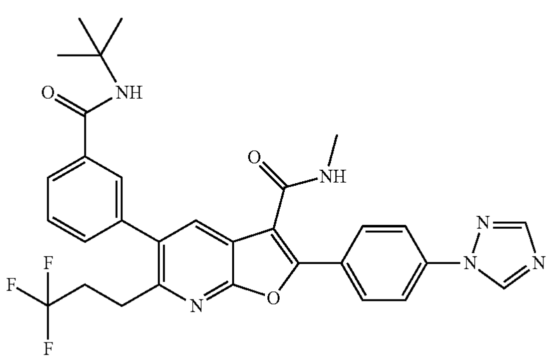 | 591.2 | 591.2 | 1.64 |

-continued

| Cmpd # | Structure | MS (M + H)+ Calcd. | MS (M + H)+ Observ. | Retention Time (min) |
|--------|-----------|--------------------|---------------------|----------------------|
| 3008 | 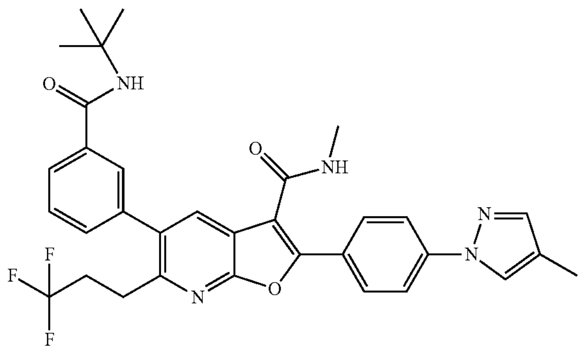 [SMILES: CNC(=O)c1c(-c2ccc(-n3cc(C)cn3)cc2)oc2nc(CCC(F)(F)F)c(-c3cccc(C(=O)NC(C)(C)C)c3)cc12] | 604.3 | 604.2 | 1.93 |
| 3009 | 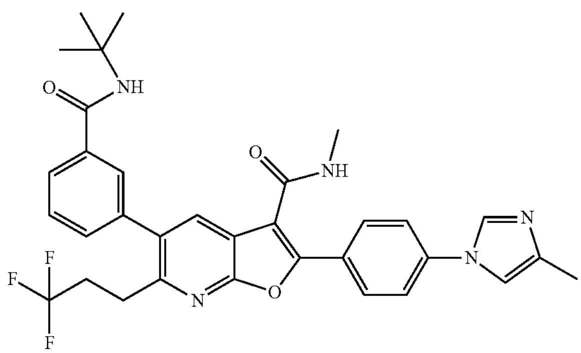 | 604.3 | 604.2 | 1.17 |
| 3010 | 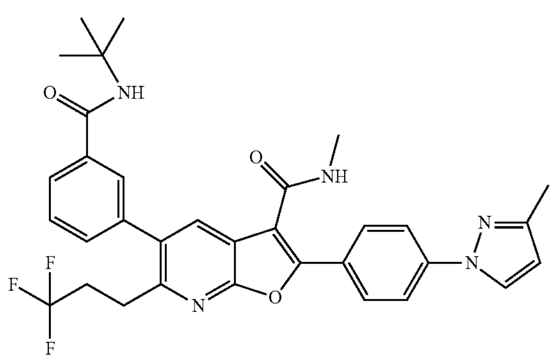 [SMILES: CNC(=O)c1c(-c2ccc(-n3ccc(C)n3)cc2)oc2nc(CCC(F)(F)F)c(-c3cccc(C(=O)NC(C)(C)C)c3)cc12] | 604.3 | 604.2 | 1.89 |

Preparation of Compound 4001:
Compound 4001 was prepared via the same procedure towards compound 3001, using pyridin-3-ol. LC condition for compound 4001 was the same for compound 3001.

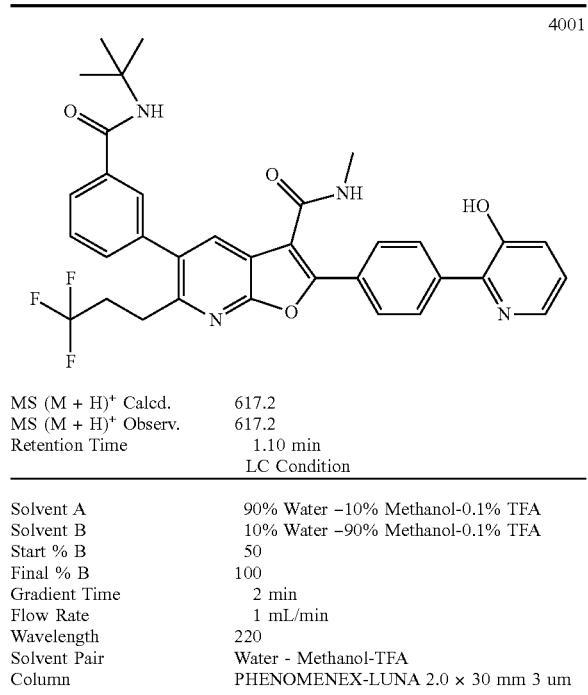

4001

| | |
|---|---|
| MS (M + H)+ Calcd. | 617.2 |
| MS (M + H)+ Observ. | 617.2 |
| Retention Time | 1.10 min |
| LC Condition | |
| Solvent A | 90% Water –10% Methanol-0.1% TFA |
| Solvent B | 10% Water –90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol-TFA |
| Column | PHENOMENEX-LUNA 2.0 × 30 mm 3 um |

Biological Methods

The compound demonstrated activity against HCV NS5B as determined in the following HCV RdRp assays.

HCV NS5B RdRp cloning, expression, and purification. The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp enzyme assay. An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo dT$_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 μL) of water, 3× reaction mix, and enzyme in 3× assay buffer (60 mM Hepes buffer, pH 7.5, 7.5 mM MgCl$_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 μM$^3$H-UTP (0.3 μCi), 1.6 U/μL RNAse inhibitor, 7 nM NS5B enzyme, 0.01 mg/mL BSA, 1 mM DTT, and 0.33 μg/μL beads, 20 mM Hepes buffer, pH 7.5, 2.5 mM MgCl$_2$, 2.5 mM KCl, and 0.1% DMSO.

Reactions were allowed to proceed for 24 hours at 30° C. and terminated by the addition of 50 mM EDTA (5 μL). After incubating for at least 15 minutes, plates were read on an Amersham LEADseeker multimodality imaging system.

IC$_{50}$ values for compounds were determined using ten different [I]. IC$_{50}$ values were calculated from the inhibition using the four-parameter logistic formula y=A+ ((B−A)/(1+ ((C/x)^D))), where A and B denote minimal and maximal % inhibition, respectively, C is the IC$_{50}$, D is hill slope and x represents compound concentration.

Cell lines. The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a Renilla luciferase reporter gene. These cells were maintained in Dulbecco's modified Eagle medium (DMEM) containing 10% FBS, 100 U/mL penicillin/streptomycin and 1.0 mg/mL G418.

HCV replicon luciferase assay. To evaluate compound efficacy, titrated compounds were transferred to sterile 384-well tissue culture treated plates, and the plates were seeded with HCV replicon cells (50 μL at a density of 2.4×10$^3$ cells/well) in DMEM containing 4% FBS (final DMSO concentration at 0.5%). After 3 days incubation at 37° C., cells were analyzed for Renilla Luciferase activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 h at 37° C. then read on a Viewlux Imager (PerkinElmer) using a luminescence program. The 50% effective concentration (EC$_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Compound $EC_{50}$ data is expressed as A:<100 nM; B=100-1000 nM; C>1000 nM). Representative data for compounds are reported in Table 2.

TABLE 2

| Cmpd # | Structure | $EC_{50}$ (uM) Ib |
|---|---|---|
| 1001 | 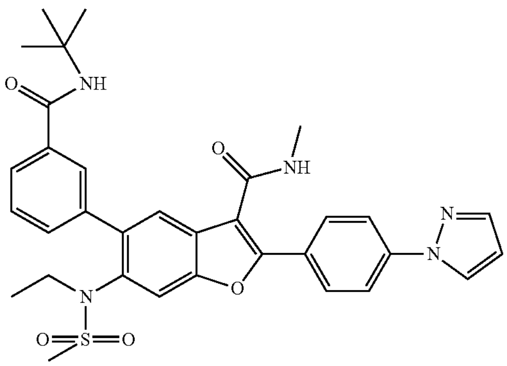 [SMILES: CCN(c1cc2oc(-c3ccc(-n4cccn4)cc3)c(C(=O)NC)c2cc1-c1cccc(C(=O)NC(C)(C)C)c1)S(C)(=O)=O] | 0.017 A |
| 1002 | 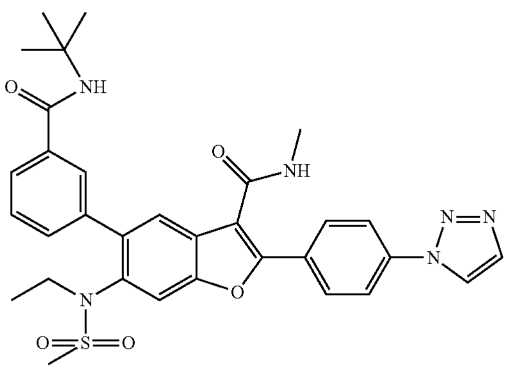 [SMILES: CCN(c1cc2oc(-c3ccc(-n4ccnn4)cc3)c(C(=O)NC)c2cc1-c1cccc(C(=O)NC(C)(C)C)c1)S(C)(=O)=O] | 0.069 A |
| 1003 | 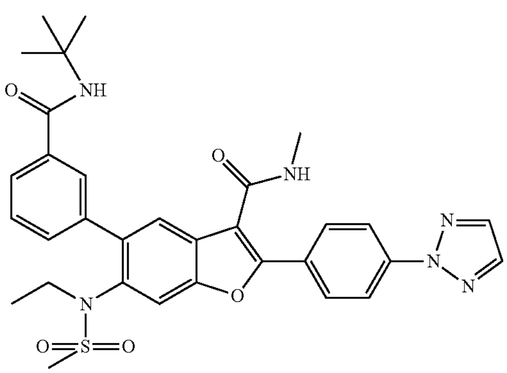 [SMILES: CCN(c1cc2oc(-c3ccc(-n4nccn4)cc3)c(C(=O)NC)c2cc1-c1cccc(C(=O)NC(C)(C)C)c1)S(C)(=O)=O] | A |
| 2001 | 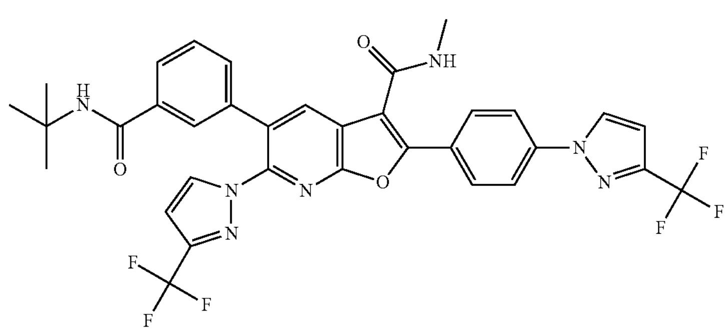 [SMILES: CNC(=O)c1c(-c2ccc(-n3ccc(C(F)(F)F)n3)cc2)oc2nc(-n3ccc(C(F)(F)F)n3)c(-c3cccc(C(=O)NC(C)(C)C)c3)cc12] | B |

TABLE 2-continued

| Cmpd # | Structure | EC$_{50}$ (µM) Ib |
|---|---|---|
| 2002 | 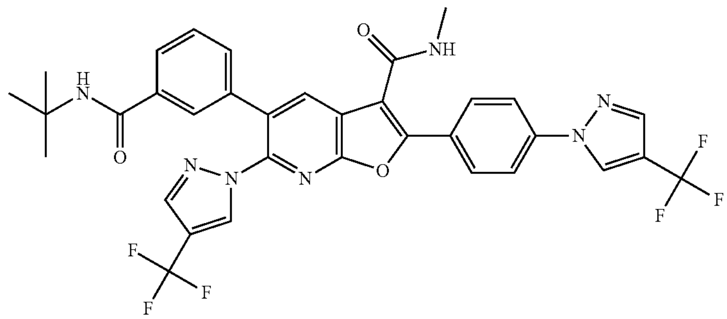 [SMILES: CNC(=O)c1c(-c2ccc(-n3cc(C(F)(F)F)cn3)cc2)oc2nc(-n3cc(C(F)(F)F)cn3)c(-c3cccc(C(=O)NC(C)(C)C)c3)cc12] | C |
| 3001 | 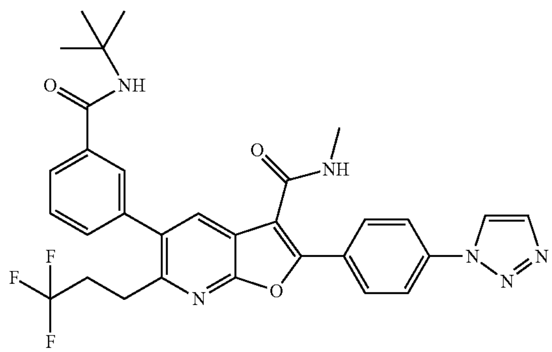 [SMILES: CNC(=O)c1c(-c2ccc(-n3ccnn3)cc2)oc2nc(CCC(F)(F)F)c(-c3cccc(C(=O)NC(C)(C)C)c3)cc12] | 0.035 A |
| 3002 | 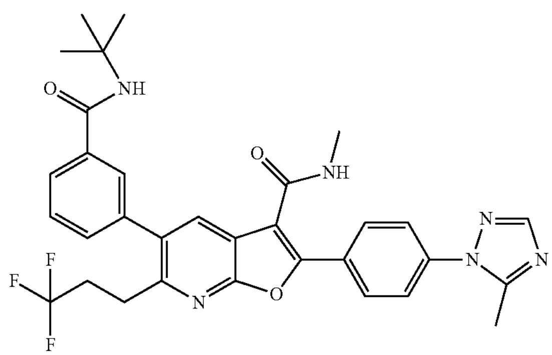 | C |
| 3003 | 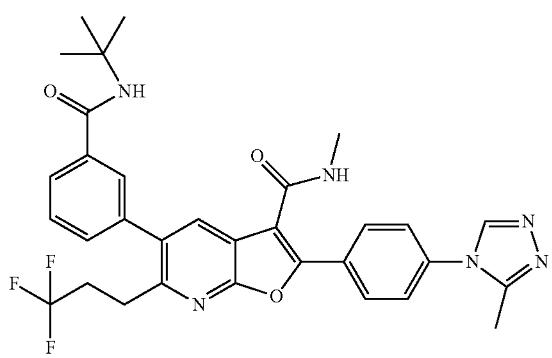 [SMILES: CNC(=O)c1c(-c2ccc(-n3cnnc3C)cc2)oc2nc(CCC(F)(F)F)c(-c3cccc(C(=O)NC(C)(C)C)c3)cc12] | 3.32 C |

TABLE 2-continued

| Cmpd # | Structure | EC$_{50}$ (uM) Ib |
|---|---|---|
| 3004 | 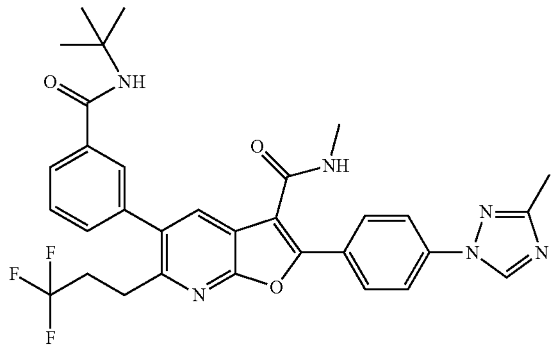 [SMILES: CNC(=O)c1c(-c2ccc(-n3cnc(C)n3)cc2)oc2nc(CCC(F)(F)F)c(-c3cccc(C(=O)NC(C)(C)C)c3)cc12] | B |
| 3006 | 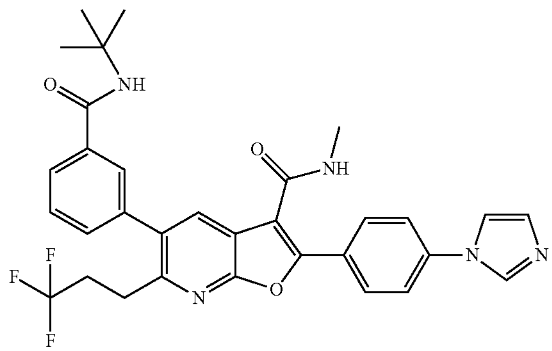 | B |
| 3007 | 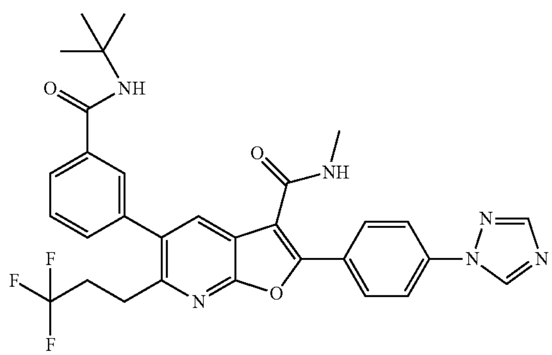 [SMILES: CNC(=O)c1c(-c2ccc(-n3cncn3)cc2)oc2nc(CCC(F)(F)F)c(-c3cccc(C(=O)NC(C)(C)C)c3)cc12] | B |
| 3008 | 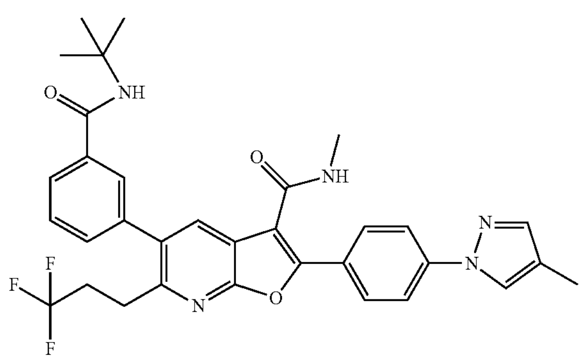 [SMILES: CNC(=O)c1c(-c2ccc(-n3cc(C)cn3)cc2)oc2nc(CCC(F)(F)F)c(-c3cccc(C(=O)NC(C)(C)C)c3)cc12] | C |

TABLE 2-continued

| Cmpd # | Structure | EC$_{50}$ (uM) 1b |
|---|---|---|
| 3009 | 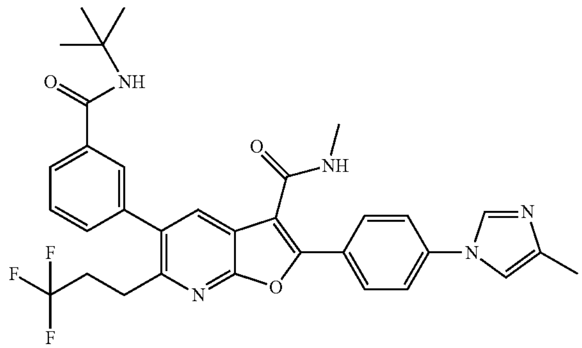 [SMILES: CNC(=O)c1c(-c2ccc(-n3cnc(C)c3)cc2)oc2nc(CCC(F)(F)F)c(-c3cccc(C(=O)NC(C)(C)C)c3)cc12] | C |
| 3010 | 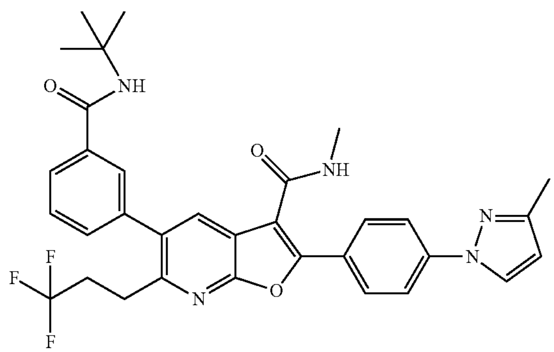 [SMILES: CNC(=O)c1c(-c2ccc(-n3ccc(C)n3)cc2)oc2nc(CCC(F)(F)F)c(-c3cccc(C(=O)NC(C)(C)C)c3)cc12] | 0.28 B |
| 4001 | 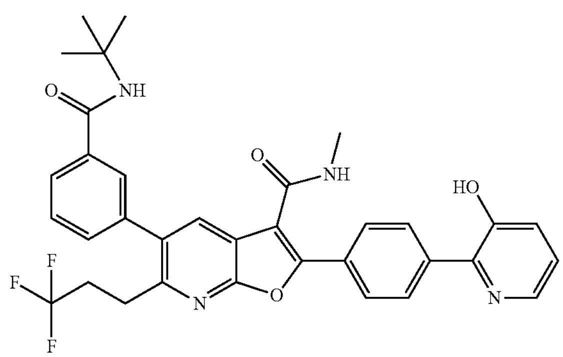 [SMILES: CNC(=O)c1c(-c2ccc(-c3ncccc3O)cc2)oc2nc(CCC(F)(F)F)c(-c3cccc(C(=O)NC(C)(C)C)c3)cc12] | B |

We claim:
1. A compound of Formula I, including pharmaceutically acceptable salts thereof:

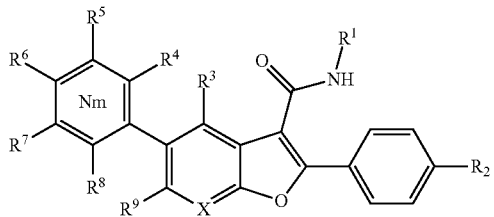

wherein
m is 0 or 1;
X is N or C—$R^{10}$;
$R^1$ is methyl;
$R^2$ is $Ar^1$;
$Ar^1$ is phenyl, 5-membered heteroaryl or 6-membered heteroaryl, and is substituted with 0-3 substituents selected from the group of cyano, halo, alkyl, cycloalkyl, haloalkyl, OH, $OR^{101}$, haloalkoxy, $NH_2$, $NR^{102}R^{103}$, $COOR^{101}$, $CONR^{102}R^{103}$, $S(O)_2R^{101}$, $S(O)_2NR^{102}R^{103}$, and $NR^{101}CONR^{102}R^{103}$;
$R^{101}$ is hydrogen, alkyl or cycloalkyl with 0-3 substituents selected from halo, hydroxyl, alkoxy, and haloalkoxy;
$R^{102}$, $R^{103}$ are each independently hydrogen, alkyl or cycloalkyl with 0-3 substituents selected from halo, hydroxyl, alkoxy, and haloalkoxy; or
$R^{102}$ and $R^{103}$ can form a ring by joining two atoms, one from each of $R^{102}$ and $R^{103}$;
$R^3$ is hydrogen, halo, or alkyl;
$R^4$, $R^5$, $R^6$, $R^7$, $R^8$ are each independently selected from the group of hydrogen, halo, alkyl, cycloalkyl, haloalkyl, halocycloalkyl, hydroxyalkyl, hydroxycycloalkyl, alkoxyalkyl, alkoxycycloalkyl, alkoxy, hydroxyalkyloxy, alkoxyalkyloxy, $COOR^{201}$ and $CON(R^{202})(R^{203})$;
$R^{201}$ is hydrogen, alkyl or cycloalkyl with 0-3 substituents selected from halo, hydroxyl, alkoxy, and haloalkoxy;
$R^{202}$, $R^{203}$ are each independently selected from the group of hydrogen, alkyl, cycloalkyl, alkenyl, cycloalkyl alkynyl, cyclic ether, cyclic amine, lactame, fused bicyclic alkyl, bridged bicyclic alkyl, spiro bicyclic alkyl, fused bicyclic ether, bridged bicyclic ether, spiro bicyclic ether, fused bicyclic amine, bridged bicyclic amine, and spiro bicyclic amine, with 0-3 substituents selected from the group of halo, OH, $OR^{104}$, $NH_2$, $NR^{105}R^{106}$, $COOR^{104}$, $CONR^{105}R^{106}$, $S(O)_2R^{104}$, $S(O)_2NR^{105}R^{106}$, $NR^{104}CONR^{105}R^{106}$, $OR^{104}CONR^{105}R^{106}$, $C(=NR^{107})NR^{105}R^{106}$, $NR^{108}C(=NR^{107})NR^{105}R^{106}$, haloalkoxy, $Ar^2$, $O-Ar^2$, and $NR^{105}-Ar^2$; or $R^{202}$ and $R^{203}$ can form a ring by joining two atoms, one from each of $R^{202}$ and $R^{203}$;
$R^{202}$ and $R^{203}$ can also form bicyclic or tricyclic rings by joining multiple atoms from each of $R^{202}$ and $R^{203}$;
$R^{104}$ is hydrogen, alkyl or cycloalkyl with 0-3 substituents selected from halo, hydroxyl, alkoxy, and haloalkoxy;
$R^{105}$, $R^{106}$ are each independently hydrogen, alkyl or cycloalkyl with 0-3 substituents selected from halo, hydroxyl, alkoxy, and haloalkoxy; or
$R^{105}$ and $R^{106}$ can form a ring by joining two atoms, one from each of $R^{105}$ and $R^{106}$;
$R^{107}$, $R^{108}$ are each independently hydrogen, alkyl or cycloalkyl with 0-3 substituents selected from halo, hydroxyl, alkoxy, and haloalkoxy; or
$R^{107}$ and $R^{108}$ can form a ring by joining two atoms, one from each of $R^{107}$ and $R^{108}$;
$Ar^2$ is phenyl, 5-membered heteroaryl or 6-membered heteroaryl, and is substituted with 0-3 substituents selected from the group of cyano, halo, alkyl, cycloalkyl, haloalkyl, OH, $OR^{204}$, haloalkoxy, $NH_2$, $NR^{205}R^{206}$, $COOR^{204}$, $CONR^{205}R^{206}$, $S(O)_2R^{204}$, $S(O)_2NR^{205}R^{206}$, and $NR^{204}CONR^{205}R^{206}$;
$R^{204}$ is hydrogen, alkyl or cycloalkyl with 0-3 substituents selected from halo, hydroxyl, alkoxy, and haloalkoxy;
$R^{205}$, $R^{206}$ are each independently hydrogen, alkyl or cycloalkyl with 0-3 substituents selected from halo, hydroxyl, alkoxy, and haloalkoxy; or
$R^{205}$ and $R^{206}$ can form a ring by joining two atoms, one from each of $R^{205}$ and $R^{206}$;
$R^9$ is selected from the group of hydrogen, halo, alkyl, cycloalkyl, alkoxy, $Ar^3$ and $NR^{301}R^{302}$;
$R^{301}$ is selected from the group of hydrogen, alkyl, cycloalkyl, (cycloalkyl)alkyl, benzyl, alkylcarbonyl, haloalkyl carbonyl, phenyl carbonyl, (alkoxyphenyl) carbonyl, alkylsulfonyl, phenylsulfonyl, (alkoxyphenyl)sulfonyl, and (haloalkoxyphenyl)sulfonyl;
$R^{302}$ is hydrogen, alkyl, hydroxyalkyl, or alkoxyalkyl; or
$R^{301}$ and $R^{302}$ taken together with the nitrogen to which they are attached is oxazolidinonyl or dioxothiazinyl;
$Ar^3$ is phenyl, 5-membered heteroaryl or 6-membered heteroaryl, and is substituted with 0-3 substituents selected from the group of cyano, halo, alkyl, cycloalkyl, haloalkyl, OH, $OR^{303}$, haloalkoxy, $NH_2$, $NR^{304}R^{305}$, $COOR^{303}$, $CONR^{304}R^{305}$, $S(O)_2R^{303}$, $S(O)_2NR^{304}R^{305}$, and $NR^{303}CONR^{304}R^{305}$;
$R^{303}$ is hydrogen, alkyl or cycloalkyl with 0-3 substituents selected from halo, hydroxyl, alkoxy, and haloalkoxy;
$R^{304}$, $R^{305}$ are each independently hydrogen, alkyl or cycloalkyl with 0-3 substituents selected from halo, hydroxyl, alkoxy, and haloalkoxy; or
$R^{304}$ and $R^{305}$ can form a ring by joining two atoms, one from each of $R^{304}$ and $R^{305}$;
$R^{10}$ is hydrogen, alkyl, halo, $N(R^{401})(R^{402})$, or alkylsulfonyl;
$R^{401}$ and $R^{402}$ are each independently selected from the group of hydrogen, alkyl, hydroxyalkyl, alkoxyalkyl, alkylsulfonyl, or alkylsulfonylalkyl;
or $N(R^{401})(R^{402})$ taken together is azetidinyl, pyrrolidinyl, piperidinyl, or piperazinyl, and is substituted with 0-2 substituents selected from alkyl, hydroxyalkyl, and hydroxy.

2. A compound of claim 1 wherein m=0.
3. A compound of claim 2 wherein $R^1$ is alkyl.
4. A compound of claim 3 wherein $R^5$ is $CON(R^{202})(R^{203})$.
5. A compound of claim 1 wherein $R^{202}$ and $R^{203}$ are hydrogen or alkyl.

6. A compound of claim 1 wherein $R^2$ is a 5-membered heteroaryl group.

7. A compound of claim 6 wherein $R^2$ has 2 to 3 nitrogens.

8. A compound of claim 1 wherein $R^9$ is selected from the group of haloalkyl, $NR^{301}$, $R^{302}$ and $Ar^3$.

9. A compound of claim 8 wherein haloalkyl is 1-3 fluoroalkyl.

10. A compound of claim 9 wherein said alkyl is propyl.

11. A compound of claim 1 wherein $R^{10}$ is hydrogen.

12. A compound, including pharmaceutically acceptable salts thereof, which is selected from the group of:

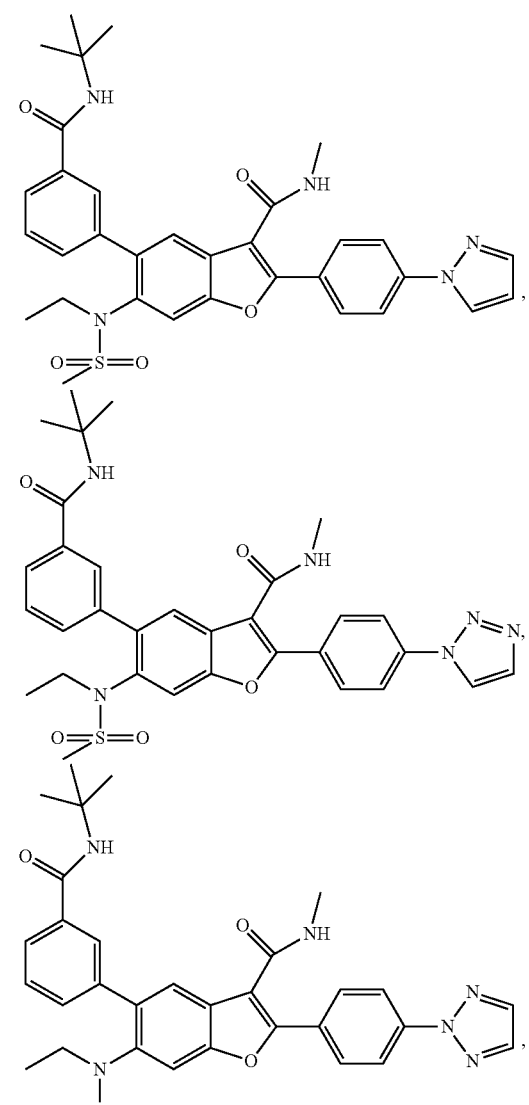

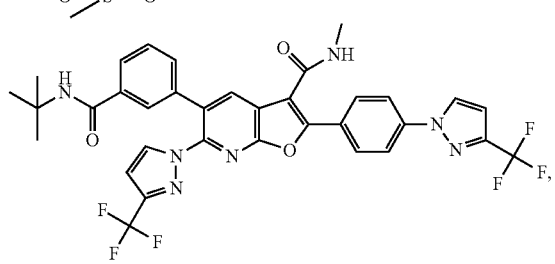

-continued

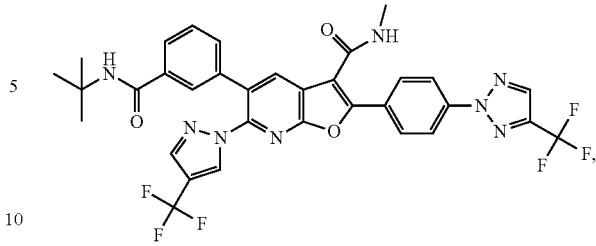

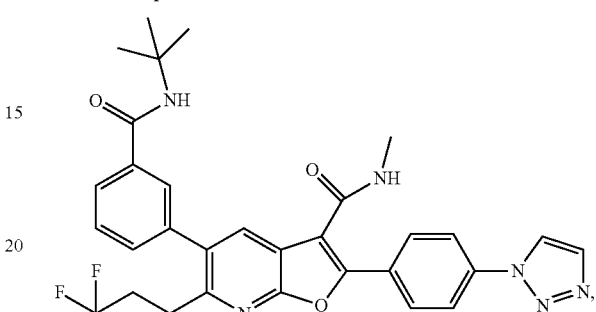

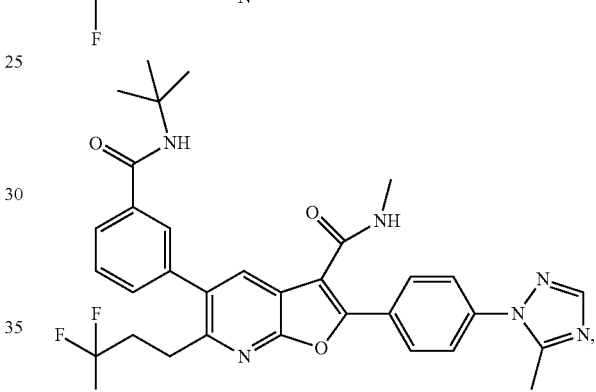

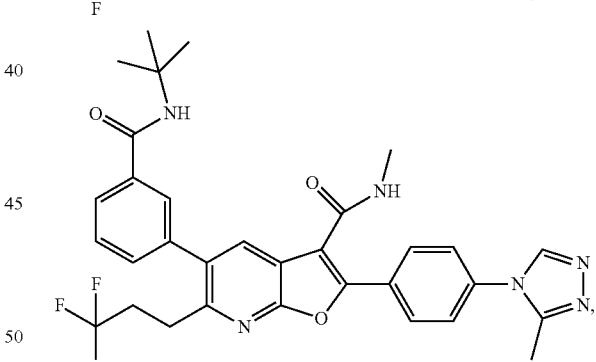

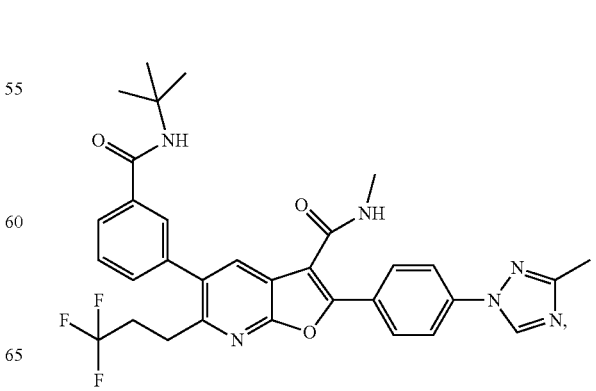

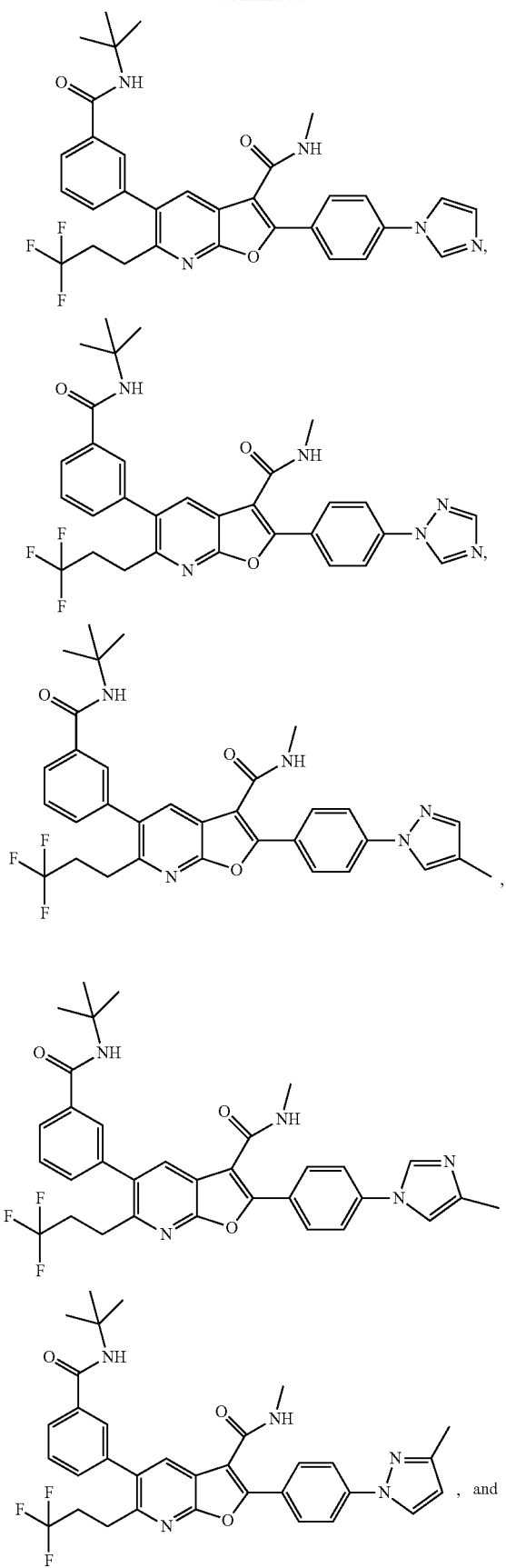
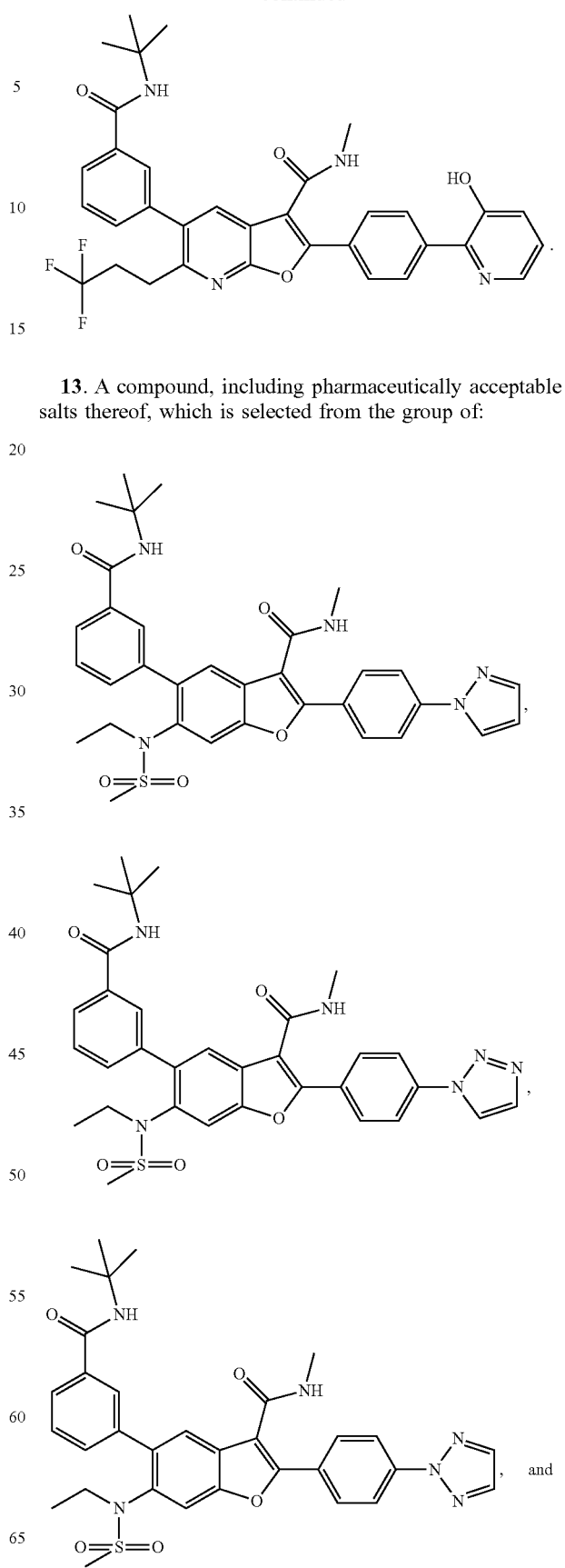
13. A compound, including pharmaceutically acceptable salts thereof, which is selected from the group of:

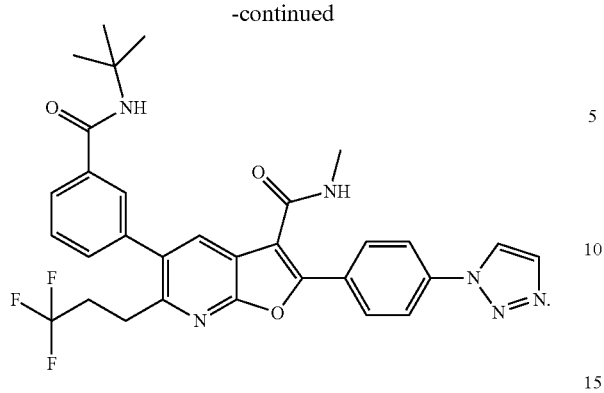

14. A composition comprising a compound of claim 1 or a pharmaceutically acceptable salt thereof and a pharmaceutically acceptable carrier, excipient, and/or diluent.

15. A composition comprising a compound of claim 12 or a pharmaceutically acceptable salt thereof and a pharmaceutically acceptable carrier, excipient, and/or diluent.

16. A composition comprising a compound of claim 13 or a pharmaceutically acceptable salt thereof and a pharmaceutically acceptable carrier, excipient, and/or diluent.

17. A compound as claimed in claim 8, wherein $R^9$ is $NR^{301}$, and $R^{301}$ is selected from alkyl and alkylsulfonyl.

* * * * *

UNITED STATES PATENT AND TRADEMARK OFFICE
CERTIFICATE OF CORRECTION

PATENT NO. : 9,840,511 B2  
APPLICATION NO. : 15/312022  
DATED : December 12, 2017  
INVENTOR(S) : Wang et al.

Page 1 of 1

It is certified that error appears in the above-identified patent and that said Letters Patent is hereby corrected as shown below:

On the Title Page

Item (73) Assignee:  
Column 1, Line 1, delete "Meyers" and insert -- Myers --.

Signed and Sealed this  
Ninth Day of October, 2018

Andrei Iancu  
*Director of the United States Patent and Trademark Office*